(12) United States Patent
Anderson

(10) Patent No.: US 9,000,773 B2
(45) Date of Patent: *Apr. 7, 2015

(54) METHOD AND APPARATUS FOR CHARACTERIZING PROCESS CONTROL EQUIPMENT INTEGRITY

(75) Inventor: Shawn W. Anderson, Haverhill, IA (US)

(73) Assignee: Fisher Controls International LLC, Marshalltown, IA (US)

( * ) Notice: Subject to any disclaimer, the term of this patent is extended or adjusted under 35 U.S.C. 154(b) by 213 days.

This patent is subject to a terminal disclaimer.

(21) Appl. No.: 13/451,432

(22) Filed: Apr. 19, 2012

(65) Prior Publication Data
US 2012/0274333 A1 Nov. 1, 2012

Related U.S. Application Data

(60) Provisional application No. 61/479,224, filed on Apr. 26, 2011.

(51) Int. Cl.
*G01R 31/02* (2006.01)
*G05B 23/02* (2006.01)
*G01N 29/09* (2006.01)
*G01N 29/14* (2006.01)
*G01N 29/24* (2006.01)
*G01N 29/34* (2006.01)
*G01N 29/44* (2006.01)
*G05B 19/042* (2006.01)

(52) U.S. Cl.
CPC ............ *G05B 23/0224* (2013.01); *G01N 29/09* (2013.01); *G01N 29/14* (2013.01); *G01N 29/245* (2013.01); *G01N 29/2475* (2013.01); *G01N 29/348* (2013.01); *G01N 29/4427* (2013.01); *G05B 19/0428* (2013.01)

(58) Field of Classification Search
USPC ............... 324/509–513; 702/76, 179, 189
See application file for complete search history.

(56) References Cited

U.S. PATENT DOCUMENTS

| | | | |
|---|---|---|---|
| 4,528,497 A * | 7/1985 | Arato | 324/509 |
| 4,783,987 A * | 11/1988 | Hager et al. | 73/32 A |
| 4,846,001 A | 7/1989 | Kibblewhite | |
| 7,937,164 B2 * | 5/2011 | Samardzija et al. | 700/28 |

(Continued)

FOREIGN PATENT DOCUMENTS

DE 198 31 372 A1 1/2000

OTHER PUBLICATIONS

International Search Report for PCT/US2012/034073, mailed Jun. 20, 2012.

(Continued)

*Primary Examiner* — Arleen M Vazquez
*Assistant Examiner* — Neel Shah
(74) *Attorney, Agent, or Firm* — Marshall, Gerstein & Borun LLP

(57) ABSTRACT

In a process plant, a first series of impedance measurements from a valve body are received. The first series of impedance measurements are stored. A second series of impedance measurements from the valve body are received. The second series of impedance measurements from the valve body are stored. The first series and second series of impedance measurements are compared. An indication of loss of integrity of the valve body is generated if the first series of impedance measurements deviates from the second series of impedance measurements.

20 Claims, 3 Drawing Sheets

(56) References Cited

U.S. PATENT DOCUMENTS

| | | | |
|---|---|---|---|
| 8,055,479 B2* | 11/2011 | Miller | 702/189 |
| 8,489,360 B2* | 7/2013 | Lundeberg et al. | 702/179 |
| 2005/0011278 A1* | 1/2005 | Brown et al. | 73/861.18 |
| 2007/0088528 A1* | 4/2007 | Miller | 702/185 |
| 2008/0082295 A1 | 4/2008 | Kant et al. | |
| 2008/0319692 A1* | 12/2008 | Davis et al. | 702/76 |
| 2009/0097537 A1 | 4/2009 | Miller | |
| 2010/0297687 A1 | 11/2010 | Mutharasan et al. | |
| 2010/0329602 A1 | 12/2010 | Shah et al. | |
| 2012/0065748 A1* | 3/2012 | Nixon et al. | 700/73 |

OTHER PUBLICATIONS

Written Opinion for PCT/US2012/034073, mailed Jun. 20, 2012.

U.S. Office Action for U.S. Appl. No. 13/451,444 dated Feb. 12, 2014.

U.S. Office Action for U.S. Appl. No. 13/451,444 dated Aug. 15, 2014.

International Search Report for PCT/US2012/034083, mailed Jul. 5, 2012.

Written Opinion for PCT/US2012/034083, mailed Jul. 5, 2012.

* cited by examiner

METHOD AND APPARATUS FOR CHARACTERIZING PROCESS CONTROL EQUIPMENT INTEGRITY

FIELD OF THE DISCLOSURE

The present disclosure relates generally to a process plants and, more particularly to monitoring the integrity of process plant components.

SUMMARY OF THE DISCLOSURE

In accordance with one exemplary aspect, a method for indicating loss of integrity of a valve body includes receiving a first series of impedance measurements, storing the first series of impedance measurements, receiving a second series of impedance measurements, storing the second series of impedance measurements, comparing the first series and second series of impedance measurements and generating an indication if the first series of impedance measurements deviates from the second series of impedance measurements.

In accordance with another exemplary aspect, a method of indicating loss of integrity of a valve body includes receiving impedance measurements by using a plurality of electrical signals at a plurality of frequencies. In accordance with yet another exemplary aspect, a method receives impedance measurements performed at frequencies that are generally in the range of 30 KHz to 400 KHz. The frequencies are applied to a PZT sensor bonded to the external surface of the valve body proximal to the closure member, in accordance with an exemplary aspect.

DETAILED DESCRIPTION

Figure 1:
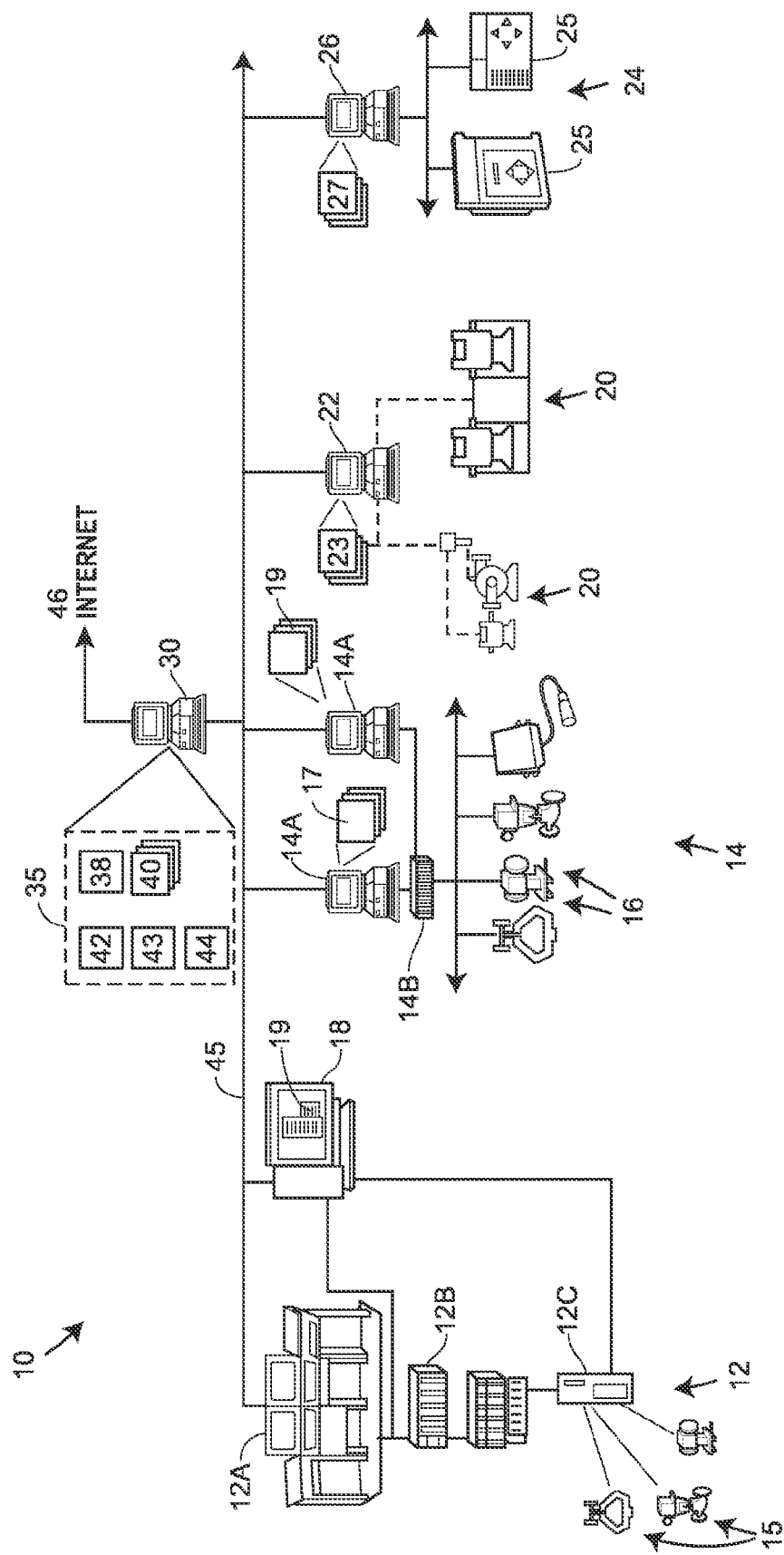
FIG. 1 is an exemplary block diagram of a process plant having a distributed control and maintenance network including one or more operator and maintenance workstations, controllers, field devices and supporting equipment, in which a fault detection and isolation system may be implemented.

Referring now to FIG. 1, an example process plant 10 in which a fault detection and isolation system may be implemented includes a number of control and maintenance systems interconnected together with supporting equipment via one or more communication networks. In particular, the process plant 10 of FIG. 1 includes one or more process control systems 12 and 14. The process control system 12 may be a traditional process control system such as a PROVOX or RS3 system or any other control system which includes an operator interface 12A coupled to a controller 12B and to input/output (I/O) cards 12C which, in turn, are coupled to various field devices such as analog and Highway Addressable Remote Transmitter (HART®) field devices 15. The process control system 14, which may be a distributed process control system, includes one or more operator interfaces 14A coupled to one or more distributed controllers 14B via a bus, such as an Ethernet bus. The controllers 14B may be, for example, DeltaV™ controllers sold by Emerson Process Management of Austin, Tex. or any other desired type of controllers. The controllers 14B are connected via I/O devices to one or more field devices 16, such as for example, HART® or Fieldbus field devices or any other smart or non-smart field devices including, for example, those that use any of the PROFI-BUS®, WORLDFIP®, Device-Net®, AS-Interface and CAN protocols. As is known, the field devices 16 may provide analog or digital information to the controllers 14B related to process variables as well as to other device information. The operator interfaces 14A may store and execute tools available to the process control operator for controlling the operation of the process including, for example, control optimizers, diagnostic experts, neural networks, tuners, etc.

Still further, maintenance systems, such as computers executing the AMS application or any other device monitoring and communication applications may be connected to the process control systems 12 and 14 or to the individual devices therein to perform maintenance and monitoring activities. For example, a maintenance computer 18 may be connected to the controller 12B and/or to the devices 15 via any desired communication lines or networks (including wireless or handheld device networks) to communicate with and, in some instances, reconfigure or perform other maintenance activities on the devices 15. Similarly, maintenance applications 17 and 19 such as the AMS application may be installed in and executed by one or more of the user interfaces 14A associated with the distributed process control system 14 to perform maintenance and monitoring functions, including data collection related to the operating status of the devices 16.

The process plant 10 also includes various rotating equipment 20, such as turbines, motors, etc. which are connected to a maintenance computer 22 via some permanent or temporary communication link (such as a bus, a wireless communication system or hand held devices which are connected to the equipment 20 to take readings and are then removed). The maintenance computer 22 may store and execute known monitoring and diagnostic applications 23 provided by, for example, CSI (an Emerson Process Management Company) or other any other known applications used to diagnose, monitor and optimize the operating state of the rotating equipment 20. Maintenance personnel usually use the applications 23 to maintain and oversee the performance of rotating equipment 20 in the plant 10, to determine problems with the rotating equipment 20 and to determine when and if the rotating equipment 20 must be repaired or replaced. In some cases, outside consultants or service organizations may temporarily acquire or measure data pertaining to the equipment 20 and use this data to perform analyses for the equipment 20 to detect problems, poor performance or other issues effecting the equipment 20. In these cases, the computers running the analyses may not be connected to the rest of the system 10 via any communication line or may be connected only temporarily.

Similarly, a power generation and distribution system 24 having power generating and distribution equipment 25 associated with the plant 10 is connected via, for example, a bus, to another computer 26 which runs and oversees the operation of the power generating and distribution equipment 25 within the plant 10. The computer 26 may execute known power control and diagnostics applications 27 such as those provided by, for example, Liebert and ASCO or other companies to control and maintain the power generation and distribution equipment 25. Again, in many cases, outside consultants or service organizations may use service applications that temporarily acquire or measure data pertaining to the equipment 25 and use this data to perform analyses for the equipment 25 to detect problems, poor performance or other issues affecting the equipment 25. In these cases, the computers (such as the computer 26) running the analyses may not be connected to the rest of the system 10 via any communication line or may be connected only temporarily.

As illustrated in FIG. 1, a computer system 30 implements at least a portion of a fault detection and isolation (FDI) system 35 using a principal component analysis (PCA) on statistical signature data. Statistical signature data may include, but is not limited to, statistical measures such as a mean, a mean change, a median, a median change, a standard deviation, a standard deviation change, a variance, a skewness, a kurtosis, a root-mean-square (RMS), a rate of change, a range, a minimum, a maximum and the like. In particular, the computer system 30 stores and implements a configuration and data collection application (CDCA) 38, one or more viewing or interface applications 40, a PCA module 42 which may include statistical processing blocks and provides multivariate statistical analysis, and a fault detection module 44. The system 30 also stores a statistical process monitoring database 43 that stores statistical signature data generated within certain devices within the process. Generally speaking, the configuration and data collection application 38 configures and communicates with each of a number of statistical data collection and analysis blocks (not shown in FIG. 1) located in the field devices 15, 16, the controllers 12B, 14B, the rotating equipment 20 or its supporting computer 22, the power generation equipment 25 or its supporting computer 26 and any other desired devices and equipment within the process plant 10, to thereby collect statistical signature data (or in some cases, raw process variable data) from each of these blocks with which to perform fault detection and isolation. The configuration and data collection application 38 may be communicatively connected via a hardwired bus 45 to each of the computers or devices within the plant 10 or, alternatively, may be connected via any other desired communication connection including, for example, wireless connections, dedicated connections which use OPC, intermittent connections, such as ones which rely on handheld devices to collect data, etc. Likewise, the configuration and data collection application 38 may obtain data pertaining to the field devices and equipment within the process plant 10 via a LAN or a public connection, such as the Internet, a telephone connection, etc. (illustrated in FIG. 1 as an Internet connection 46) with such data being collected by, for example, a third party service provider. Further, the configuration and data collection application 38 may be communicatively coupled to computers/devices in the plant 10 via a variety of techniques and/or protocols including, for example, Ethernet, Modbus, HTML, XML, proprietary techniques/protocols, etc. Thus, although particular examples using OPC to communicatively couple the configuration and data collection application 38 to computers/devices in the plant 10 are described herein, one of ordinary skill in the art will recognize that a variety of other methods of coupling the configuration and data collection application 38 to computers/devices in the plant 10 can be used as well. The collected data may be reference data, associated with a known normal or known abnormal process condition, or monitored data, for which the process condition is unknown. The configuration and data collection application 38 may generally store the collected data in the database 43.

Although the process plant 10 is shown as including an FDI system 35, it should be understood that the FDI system 35 is not limited to detecting of existing faults or other abnormal conditions, but may also predict the occurrence of an abnormal condition, examples of which as disclosed further below. As such, the FDI system 35 may be utilized to detect existing faults and other abnormal conditions within the process as part of fault detection and isolation, and to predict the occurrence of faults and other abnormal conditions within the process as part of abnormal condition prevention. For example, the fault detection module 44 may be utilized to detect existing and predicted abnormal conditions, as described herein.

Further, although PCA is primarily disclosed as a multivariate statistical analysis technique that may be employed, it should be understood that PCA is provided only as an example, and PCA is explained in order to better understand the fault detection and abnormal condition prevention methodology employed. As such, other multivariate statistical analysis techniques may also be utilized, including, but not limited to partial least squares (PLS), principal component regression (PCR), discriminant analysis and canonical variate analysis (CVA). Different multivariate statistical analysis techniques may be utilized depending on the abnormal condition being detected. For example, while PCA may be utilized for both detecting and predicting abnormal conditions, PCA may be utilized to detect the occurrence of abnormal conditions whereas PLS and/or PCR may be utilized to predict the occurrence of abnormal conditions. As such, the FDI system 35 may include additional modules for different multivariate analysis techniques and/or the PCA module 42 may be replaced with a PLS module, a PCR module, a discriminant analysis module, a CVA module or any other multivariate statistical analysis module.

Referring again to FIG. 1, once the configuration and data collection application 38 collects the statistical signature (or raw process variable) data, the PCA module 42 may conduct multivariate statistical analysis to process the data in one of several ways. The PCA module 42 may use the collected statistical signature data as reference data associated with a normal condition and one or more abnormal conditions, to determine principal components associated with more than one process condition, and form a loading matrix associated with the combined conditions. Alternatively, the PCA module 42 may use the collected statistical signature data as reference data, associated with a normal or abnormal process condition, to determine principal components associated with the process condition, and form a loading matrix associated with each condition. The PCA module 42 may also use raw process variable data, if associated with a known normal or known abnormal process condition, to compute reference statistical signature data from which to determine principal components associated with one or more process conditions. Raw process variable data may include, but is not limited to, data measured from the process including data measured from devices within the process such as temperature, pressure, flow rate, position and the like. The PCA module 42 may further store the results of the principal component analysis, as well as the reference statistical signature data in the database 43 for use by the fault detection module 44 or the viewing application 40. Additionally, the PCA module 42 may determine, using parallel analysis or another similar method, how many principal components calculated by the PCA module 42 to retain for use by the fault detection module 44.

The fault detection module 44 analyzes monitored statistical signature (or raw process variable) data, using the results of the principal component analysis performed by the PCA module 42, to determine the existence or future existence of an abnormal process condition. As described in detail below, the fault detection module 44 may project the monitored statistical signature or raw process variable data into the score matrix, using the loading matrix previously determined by the PCA module 42. The fault detection module 44 may then generate one or more alerts or alarms for operators or maintenance personnel based on the results of the analysis, or otherwise alert process operators or maintenance personnel that an abnormal condition exists or is predicted. Likewise, the fault detection module 44 may store the results of the analysis, including faults detected, alerts or alarms generated, and data projected onto the score matrix (described below), in the database 43 or communicate the results to the viewing and interface application 40.

The viewing and interface application 40 includes an interface for plant personnel such as configuration engineers, process control operators, maintenance personnel, plant managers, supervisors, etc. to view alerts and alarms generated by the fault detection module 44. The viewing application 40 may also include an interface that allows manipulation of various process control parameters, manipulation of the PCA module 42 and the fault detection module 44, and display of relevant data including statistical signature data, raw process variable data, auto-scaled data, data mapped on to score matrices or any other data useful to display for plant personnel.

The viewing and interface application 40 may provide a graphical user interface (GUI) that is integrated with the system 30, or more particularly with the FDI system 35, to facilitate a user's interaction with the monitoring capabilities provided by the FDI system 35. However, before discussing the GUI in greater detail, it should be recognized that the GUI may include one or more software routines that are implemented using any suitable programming languages and techniques. Further, the software routines making up the GUI may be stored and processed within a single processing station or unit, such as, for example, a workstation, a controller, etc. within the plant 10 or, alternatively, the software routines of the GUI may be stored and executed in a distributed manner using a plurality of processing units that are communicatively coupled to each other within the FDI system 35.

Preferably, but not necessarily, the GUI may be implemented using a familiar graphical windows-based structure and appearance, in which a plurality of interlinked graphical views or pages include one or more pull-down menus that enable a user to navigate through the pages in a desired manner to view and/or retrieve a particular type of information. The features and/or capabilities of the FDI system 35 may be represented, accessed, invoked, etc. through one or more corresponding pages, views or displays of the GUI. Furthermore, the various displays making up the GUI may be interlinked in a logical manner to facilitate a user's quick and intuitive navigation through the displays to retrieve a particular type of information or to access and/or invoke a particular capability of the FDI system 35.

Those of ordinary skill in the art will appreciate that the FDI system 35 described herein may operate alone or in cooperation with other systems, including other fault detection and abnormal condition prevention systems. Likewise, the individual applications 38, 40, 42, and 44 described herein as part of the FDI system 35 may operate cooperatively with other applications (not shown) to detect faults, generate alerts and alarms, provide data to plant personnel, allow process or device configuration or any combination of the above.

Referring again to FIG. 1, valves 15 and 16 for example may be used to control the flow rate of materials in a semi-solid, liquid or gaseous state in the process plant. In some instances the materials may include suspended particulate material. In other instances, the materials may interact with the body of the valves 16 for example causing the valve body to corrode overtime. Suspended particulate matter may abrade the inner surface of the valve body causing erosion damage. Process fluid properties and pressure drop combinations may cause fluid cavitation which may also erode the valve body material internally.

In some instances, the valve body may be adapted with sensors. Such sensors include but are not limited to piezoelectric (PZT) sensors for example. Sensors employed may be active or passive. Active sensors generally are provided with an external excitation signal. Passive sensors generally are not provided with an external excitation signal. The sensors may be bonded to the valve body, in some instances. In other instances, the valve body may be manufactured with the sensor in the valve body. In such instances the valves may be provided with a port to access the sensor. In certain instances, the sensors are monitored and controlled by statistical data collection and analysis blocks which may be located at valve positioners or the valve bodies 15 for example. In this instance, the sensor is adapted with a connector bus which is adapted to receive power, excitation signals and transmit electrical sensor data to the data collection block. In other instances the sensors may be monitored and controlled from I/O cards 12C for example. In some instances the data received by the data collection and analysis block is also received by the FDI 35.

In some embodiments the PCA module 42 analysis the data from a sensor bonded to the valve body. In this embodiment, the PCA module 42 provides real-time monitoring of the integrity of the valve body. Detecting of cavitations may be automated by the PCA module 42 without requiring a visual inspection of the valve body. The PCA module 42 in this embodiment creates a signature from the data received from the sensor bonded to the valve body. In other embodiments the sensor data from a valve body is analyzed by an AMS system for example.

Figure 2:
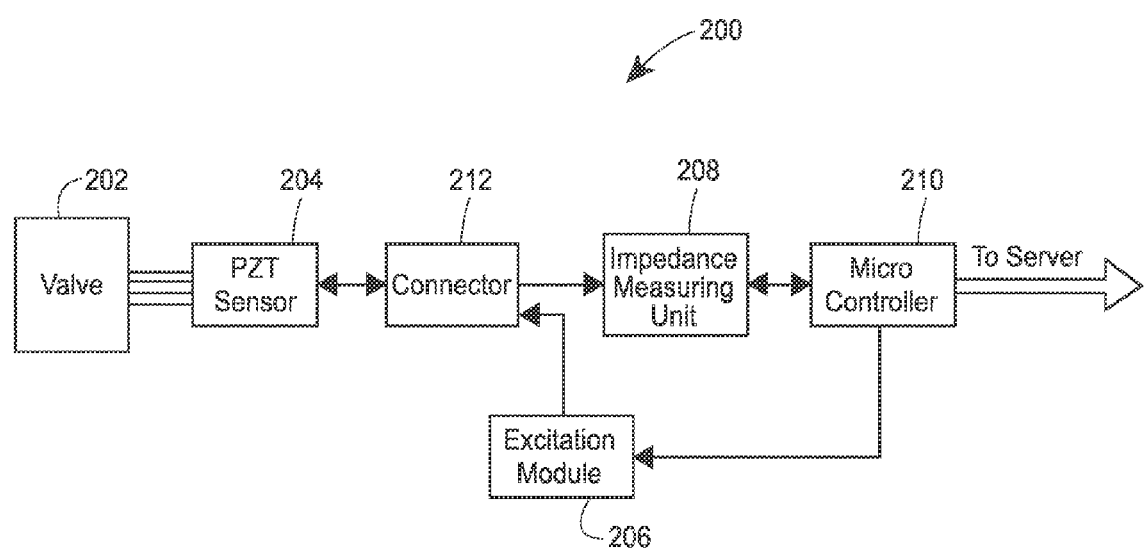
FIG. 2 is a block diagram of a statistical data collection and analysis block implementing a method to detect changes in integrity of a valve body.

FIG. 2 is a block diagram of a statistical data collection and analysis block located in the field devices 15, 16 for example that implements an embodiment 200 to detect structural changes of a valve 16, for example. In this embodiment, a piezoelectric (PZT) sensor 204 is attached to a valve body 202 using a suitable bonding technique. The PZT sensor 204 is made from a piezoceramic material such as lead zirconate titanate, in this embodiment. One skilled in the art will recognize that any material exhibiting a piezoelectric effect may be used as a sensor. The PZT sensor 204 is soldered to the valve body 202, in this embodiment. In some other embodiment, the sensor 204 is attached to the valve body 202 with a bonding agent or adhesive. In yet other embodiment, the sensor 204 is integrated in the valve body 202. In this embodiment, access to the sensor 204 is provided through connector 212.

In this embodiment, the PZT sensor 204 is provided with an excitation frequency by an excitation module (EM) 204. In this embodiment, EM 204 is controlled by microcontroller 210. The microcontroller 210 communicates with the EM 204 over a serial I2C bus in this embodiment. The EM 204 is adapted to generate electrical signals having excitation frequencies that range from 30-400 Kilohertz (KHz), in this embodiment. In this embodiment, the microcontroller 210 communicates to the EM 204 the desired excitation frequency to be generated. Also, in this embodiment, the microcontroller 210 provides the EM 204 the desired voltage level for the electrical signals generated by the EM 204. In another embodiment, the microcontroller 210 provides the EM 204 the range of excitation frequencies to be generated. In this embodiment, the EM 204 sequentially generates electrical signals having excitation frequencies corresponding to the range of excitation frequencies provided by the microcontroller.

In an embodiment, the EM 204 comprises a digital to analog convertor (DAC) electrical coupled to a voltage controlled oscillator (VCO). In this embodiment, the DAC receives a digital representation of the excitation frequency from the microcontroller 210. The DAC produces an analog voltage which corresponds to the excitation frequency for electrical signal to be generated. The VCO generates the excitation frequency that corresponds to the analog voltage produced by the DAC, in this embodiment. In some other embodiments, the EM 204 is adapted to generate electrical signals complex having two or more excitation frequencies.

On receiving an electrical signal from the EM 204, the PZT 204 generates an electrical current that corresponds to the impedance measure of the combined PZT 204 and valve body 202. The electrical current generated by the PZT 204 changes as the excitation frequency of the electrical signal generated by the EM 204 is changed.

The electrical current generated by the PZT 204 is received by an impedance measuring unit (IMU) 208. The IMU 208 communicates with the microcontroller 210 over a serial I2C bus. The microcontroller 210 instructs the IMU 208 to sample the electrical current generated by the PZT 204. The IMU 208 comprises signal conditioning circuitry and electronics. Such circuitry includes but is not limited to current to voltage convertors, low noise amplifiers (LNA), band pass and notch filters. One skilled in the art will recognize that the impedance measure comprises real and imaginary components. The IMU 208 generates a digital representation of the real component of the electrical current that corresponds to the impedance measure of the combined PZT 204 and valve body 202, in this embodiment. The digital representation of the impedance measure of the combined PZT 204 and the valve body 202 is received by the microcontroller 210. In an embodiment the IMU 208 comprises an analog to digital convertor (ADC). In this embodiment, the ADC is a successive approximation ADC. In another embodiment, a dual slope ADC is employed.

In an embodiment, the microcontroller 210 communicates to the EM 204 the desired excitation frequency of the electrical signal to be generated. The EM 204 generates an electrical signal at the excitation frequency and applies the electrical signal to the PZT 204. The microcontroller 210 instructs the IMU 208 to sample the electrical current generated by the PZT 204 in response to the electrical signal. The digital representation is received by the microcontroller 210. The microcontroller 210 communicates to the EM 204 a different excitation frequency for the electrical signal to be generated and instructs the IMU 208 to sample the electrical current generated by the PZT 204 in response to receiving the electrical signal generated at the different excitation frequency. In this embodiment, the microcontroller sequentially communicates to the EM 204 excitation frequencies that range from 30-400 KHz in steps of 1 KHz for example 30 KHz, 31 KHz . . . , 399 KHz, and 400 KHz. After communicating each excitation frequency to the EM 204, the microcontroller 202 instructs the IMU 208 to sample the electrical current generated by the PZT 204 in response to receiving the electrical signal generated at the different excitation frequency. Thus, the microcontroller 210 creates an impedance record of the impedance measure of the combined PZT 204 and valve body 202 and the corresponding excitation frequencies of the electrical signals generated by the EM 206.

Referring to FIG. 1, the microcontroller 210 transmits the record comprising impedance measures and the corresponding excitation frequencies to a computer system 30, in an embodiment. In this embodiment, the microcontroller 210 implements the CAN protocol to communicate with the computer system 30. In this embodiment, the CDCA 38 implemented as a part of fault detection and isolation (FDI) system 35 which in turn is implemented at computer system 30 instructs the microcontroller 210 to create an impedance record. The CDCA 38 instructs the microcontroller 210 of the start excitation frequency, the end excitation frequency and the incremental change in frequency. The CDCA 38 receives the impedance record from the microcontroller 210. In this embodiment, the CDCA 38 stores the impedance record in the database 43.

The PCA module 42 retrieves the stored impedance record from the database 43 and applies curve fitting techniques to the impedance record. In an embodiment, the PCA module 42 generates an nth order polynomial fit of the impedance record. The PCA module 42 stores the coefficients of the polynomial in the database 43. In an embodiment, these coefficients correspond to the impedance signature of the valve body 202, for example. In other embodiment, the impedance record serves as the impedance signature of the valve body 202, for example.

In an embodiment, the CDCA 38 periodically instructs the microcontroller 210 to create an impedance record. The CDCA 38 receives the impedance record from the microcontroller 210.

In an embodiment, the CDCA 38 receives the impedance record and retrieves a prior stored impedance record for the valve body 202, for example. In this embodiment the CDCA 38 communicates the received impedance record and the retrieved impedance record to the PCA 42. The PCA 42 compares the impedance records to detect a change in the impedance signature. In one embodiment, the impedance record is compared to an as-built/as-new impedance record. In an embodiment, a change is signaled if the coefficients calculated for a polynomial fit of the impedance record deviate from preset thresholds for the coefficients. In some embodiments, the PCA 42 computes an average of the historical impedance records stored in database 43 for a valve body 202, for example. The average of the impedance records is compared with a received impedance record to detect deviations from the average. In still other embodiments, the PCA 42 computes a standard deviation of an impedance record received from the CDCA 38 from the historical impedance records stored in the database 43.

In this embodiment, a user specifies a threshold standard deviation value in the viewing and interface application 40 that is integrated with the system 30, or more particularly with the FDI system 35. If the received impedance record deviates from the user-specified threshold, an indication in the form of a visual cue and an audible sound are generated in this embodiment. In this embodiment, a deviation indicates a loss of valve body material or a discontinuity in the form of a crack.

In an embodiment, a user instructs the microcontroller 210 to create an impedance record through the viewing and interface application 40. In some embodiments, the FDI system 35 provides a user with an indication corresponding to the useful life of the valve body 202, for example. In this embodiment, the indication is provided via the viewing and interface application 40.

Referring to FIG. 2, one skilled in the art will recognize that in some embodiments the FDI 35 is implemented at the microcontroller 210. In such an embodiment, the system 200 comprises a standalone system to monitor the integrity of valve body 202.

In some embodiments, a PZT sensor may be employed in a passive mode. In this mode of operation, the PZT sensor is not provided with an excitation signal. In this embodiment, the PZT sensor detects audible changes resulting from structural changes, in a valve for example. The audible changes may be produced by acoustic emissions from propagating cracks in the material of the valve.

In an embodiment, a PZT sensor detects failure of a valve body, for example. In this embodiment, a microcontroller 210 causes an impedance measuring unit 208 to sense the audible level detected by a sensor 204, for example. In this embodiment, a FDI 35 generates a signature based on the audible level received from the microcontroller 210. In this embodiment, the FDI 35 configures a threshold for the audible level at microcontroller 210. Microcontroller 210 generates an indication when the audible signal exceeds the threshold. A change in the audible signal corresponds to structural changes in the valve, in an embodiment. The structural change may include failure of the valve body or clogging of the valve, for example. In this embodiment, the FDI 35 asynchronously receives an indication when the microcontroller detects a change in the audible level that exceeds the threshold. The FDI 35, in this embodiment, may generate an alarm or modify the operation of the process plant. In any embodiments, the FDI 35 implements suitable algorithms to analyze the frequencies and energy levels of the acoustic emissions.

Figure 3:
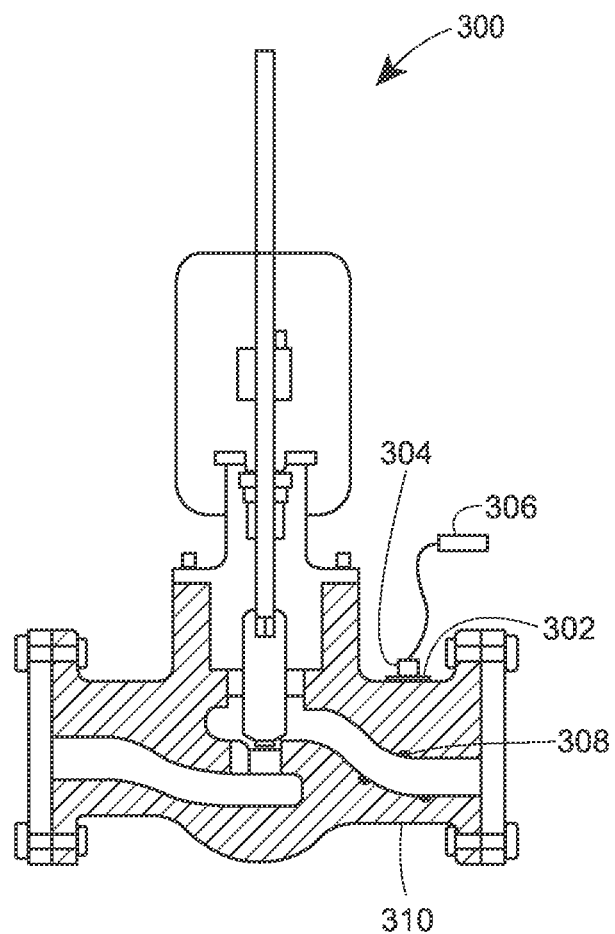
FIG. 3 is a cross-sectional diagram of a valve body depicting the possible location of a PZT sensor from which impedance measurements may be received.

FIG. 3 is a transverse cross of an example valve body 202. Referring to FIG. 1, the valve 300 corresponds to the valve 15 in an embodiment. In this embodiment, the PZT sensor 304 is bonded to the valve body 310 near the closure member. The PZT sensor 304 is bonded with a suitable bonding agent. The PZT sensor 304 is adapted with an electrical connector 306. The connector 306 corresponds to the connector 212 in an embodiment. The valve body 310 exhibits cavitations 308 which may result in loss of valve body material. In this embodiment, the impedance record received by the CDCA 38 deviates from the historical impedance records of the valve body 310 before the occurrence of cavitations 308. An alarm indicating loss of valve body integrity is indicated at the GUI that is integrated with the system 30, in this embodiment.

In another embodiment, a CDCA 38 receives impedance records from a PZT sensor bonded to actuator legs. Deviation of a received impedance record from a historical impedance record for the actuator legs causes the generation of an event indicating fatigue cracking of the actuator legs, in an embodiment. Referring to FIG. 3, in another embodiment, the valve 300 may be used to convey solid or semi-solid materials for example sludge or coke. In this embodiment, deviation of an impedance record from a historical impedance record may indicate a plugging of the valve.

In yet another embodiment, a plurality of PZT sensors 304 may be bonded to a valve body 310. In this embodiment, impedance records comprising sequential excitations of the plurality of sensors may be received. In this embodiment, CDCA 38 may develop a three dimensional map of the integrity of the valve body.

What is claimed is:

1. A method implemented at a fault detection and isolation (FDI) system for indicating loss of integrity of a body of a field device, the method comprising:
receiving at the FDI system a first series of measurements from the field device;
storing the first series of measurements;
receiving at the FDI system a second series of measurements from the field device;
storing the second series of measurements;
generating a first curve based on the first series of measurements and a second curve based on the second series of measurements;
determining a first plurality of coefficients for the first curve and a second plurality of coefficients for the second curve;
comparing the first plurality of coefficients and the second plurality of coefficients to determine if the first series of measurements deviates from the second series of measurements;
generating an indication if the first plurality of coefficients deviates from the second plurality of coefficients.

2. The method of claim 1, wherein the first series of measurements and the second series of measurements comprise impedance measurements.

3. The method of claim 1, wherein the first series of measurements and the second series of measurements comprise acoustic measurements.

4. The method of claim 2, wherein the first series of impedance measurements and the second series of impedance measurements are made using a plurality of electrical signals at a plurality of frequencies, the impedance measurements made in response to the FDI transmitting a first request for the first series of impedance measurements and a second request for the second series of impedance measurements.

5. The method of claim 4, wherein transmitting the first request and the second request includes transmitting an indication of at least one of the plurality of frequencies.

6. The method of claim 4, wherein each of the plurality of frequencies range from 30 Kilohertz (KHz) to 400 KHz.

7. The method of claim 4, wherein the field device is a valve including a closure member, and applying the plurality of electrical signals to the valve body through a piezoelectric (PZT) sensor.

8. The method of claim 7, including bonding the PZT sensor to the valve body near the valve body closure member.

9. The method of claim 7, including bonding the PZT sensor to the valve body with an adhesive.

10. The method of claim 3, wherein the first series and the second series of acoustic measurements comprise measurements received from a PZT sensor in response to the FDI transmitting a first request for the first series of acoustic measurements and a second request for the second series of acoustic measurements.

11. An apparatus for detecting the loss of integrity of a body of a field device, the apparatus comprising:
a fault detection and isolation (FDI) system;
a sensor coupled to the body of the field device;
an excitation module electrically coupled to the sensor;
a measurement module electrically coupled to the sensor;
an analyzer coupled to the measurement module and configured to generate a first curve based on a first series of measurements by the measurement module and a second curve based on a second series of measurements by the measurement module, the analyzer further configured to determine a first plurality of coefficients for the first curve and a second plurality of coefficients for the second curve and then compare the first plurality of coefficients and the second plurality of coefficients to determine if the first series of measurements deviates from the second series of measurements; and
an indicator coupled to the analyzer and configured to generate an indication if the first plurality of coefficients deviates from the second plurality of coefficients.

12. The apparatus of claim 11, wherein the sensor is a piezoelectric (PZT) sensor.

13. The apparatus of claim 12, wherein the PZT sensor is coupled to the body of the field device near a closure member of the field device with a bonding adhesive.

14. The apparatus of claim 13, wherein the excitation module is arranged to electrically excite the PZT sensor via the electrical coupling with an electrical signal at a selected frequency, wherein the selected frequency ranges from 30 Kilohertz (KHz) to 400 KHz.

15. The apparatus of claim 14, wherein the excitation module is arranged to receive an indication of the selected frequency from the FDI.

16. The apparatus of 15, wherein the measurement module is arranged to transmit data measured from the PZT sensor to the FDI.

17. A method for indicating loss of integrity of a body of a field device, the method comprising:
   causing a fault detection and isolation (FDI) system to receive a first series of measurements, wherein each of the measurements of the first series of measurements is made at the body of the field device;
   in response to receiving the first series of measurements, causing the FDI system to store the first series of measurements;
   causing the FDI system to receive a second series of measurements, wherein each of the measurements of the second series of measurements is made at the body of the field device;
   in response to receiving the second series of measurements, causing the FDI system to store the second series of measurements;
   generating a first curve based on the first series of measurements and a second curve based on the second series of measurements;
   determining a first plurality of coefficients for the first curve and a second plurality of coefficients for the second curve;
   comparing the first plurality of coefficients and the second plurality of coefficients to determine if the first series of measurements deviates from the second series of measurements;
   determining that the first plurality of coefficients deviates from the second plurality of coefficients; and
   causing the FDI to generate an indication on determining that the first plurality of coefficients deviates from the second plurality of coefficients.

18. The method of claim 17, wherein the first series of measurements is received in response to causing the FDI system to transmit a first request for the first series of measurements and the second series of measurements is received in response to causing the FDI system to transmit a second request for the second series of measurements.

19. The method of claim 18, wherein each of the first request and the second request includes an indication of a selected frequency.

20. The method of claim 19, wherein each of the first series of measurements and the second series of measurements correspond to impedance measurements caused to be made at body of the field device by exciting a PZT sensor with an electrical signal at the selected frequency, wherein the PZT sensor is bonded to the body of the field device.

* * * * *